United States Patent
Sjökvist

(10) Patent No.: US 10,384,018 B2
(45) Date of Patent: Aug. 20, 2019

(54) SAFETY INJECTION NEEDLE DEVICE

(71) Applicant: Arta Plast AB, Tyresö (SE)

(72) Inventor: Sven Ingvar Sjökvist, Tyresö (SE)

(73) Assignee: Arta Plast AB, Tyresö (SE)

(*) Notice: Subject to any disclaimer, the term of this patent is extended or adjusted under 35 U.S.C. 154(b) by 116 days.

(21) Appl. No.: 15/455,757

(22) Filed: Mar. 10, 2017

(65) Prior Publication Data
US 2017/0259009 A1    Sep. 14, 2017

(30) Foreign Application Priority Data

Mar. 11, 2016 (SE) ...................... 1650335

(51) Int. Cl.
*A61M 5/32* (2006.01)

(52) U.S. Cl.
CPC ........ *A61M 5/3245* (2013.01); *A61M 5/3204* (2013.01); *A61M 5/326* (2013.01); *A61M 5/3293* (2013.01); *A61M 2005/3247* (2013.01); *A61M 2005/3267* (2013.01)

(58) Field of Classification Search
CPC .. A61M 2005/3247; A61M 2005/3267; A61M 2005/3268; A61M 2005/3246
See application file for complete search history.

(56) References Cited

U.S. PATENT DOCUMENTS

| | | | | |
|---|---|---|---|---|
| 3,874,383 A * | 4/1975 | Glowacki | ............... | A61M 5/32 604/110 |
| 4,795,432 A * | 1/1989 | Karczmer | ........... | A61M 5/3257 604/110 |
| 4,894,055 A * | 1/1990 | Sudnak | ............... | A61M 5/3271 604/110 |
| 6,869,415 B2 * | 3/2005 | Asbaghi | ............ | A61B 5/15003 604/110 |
| 9,694,140 B2 * | 7/2017 | Rubinstein | ............ | A61M 5/326 |
| 10,179,211 B2 * | 1/2019 | Rozwadowski | . | A61B 5/150183 |
| 2007/0293819 A1 | 12/2007 | Giambattista et al. | | |
| 2008/0077093 A1 | 3/2008 | Gratwohl et al. | | |
| 2009/0221972 A1 | 9/2009 | Gratwohl et al. | | |
| 2009/0259196 A1 | 10/2009 | Gratwohl et al. | | |
| 2009/0326477 A1 * | 12/2009 | Liversidge | ............ | A61M 5/326 604/198 |
| 2010/0234811 A1 * | 9/2010 | Schubert | ............... | A61M 5/326 604/198 |
| 2010/0292654 A1 | 11/2010 | Schraga | | |
| 2011/0257603 A1 * | 10/2011 | Ruan | ..................... | A61M 5/326 604/198 |
| 2014/0243752 A1 | 8/2014 | Hsu et al. | | |
| 2015/0011944 A1 * | 1/2015 | Young | ................. | A61M 5/2033 604/198 |

OTHER PUBLICATIONS

Corresponding European application, application No. 17160307.9, European Search Report dated Jul. 17, 2017, 9 pages.

* cited by examiner

*Primary Examiner* — William R Carpenter
(74) *Attorney, Agent, or Firm* — Cooper Legal Group, LLC; Ronald M. Kachmarik

(57) ABSTRACT

A safety injection needle device for delivery of a medicament from a storage reservoir with longitudinal axis A. The device includes: a device body; a needle; a needle shield device, and a spring. A rear end of the needle shield device is made of a deformable material such that at least a section of the rear end of the needle shield device is deformed such that the radius of the rear end is increased such that the needle shield device is locked in the extracted position.

16 Claims, 4 Drawing Sheets

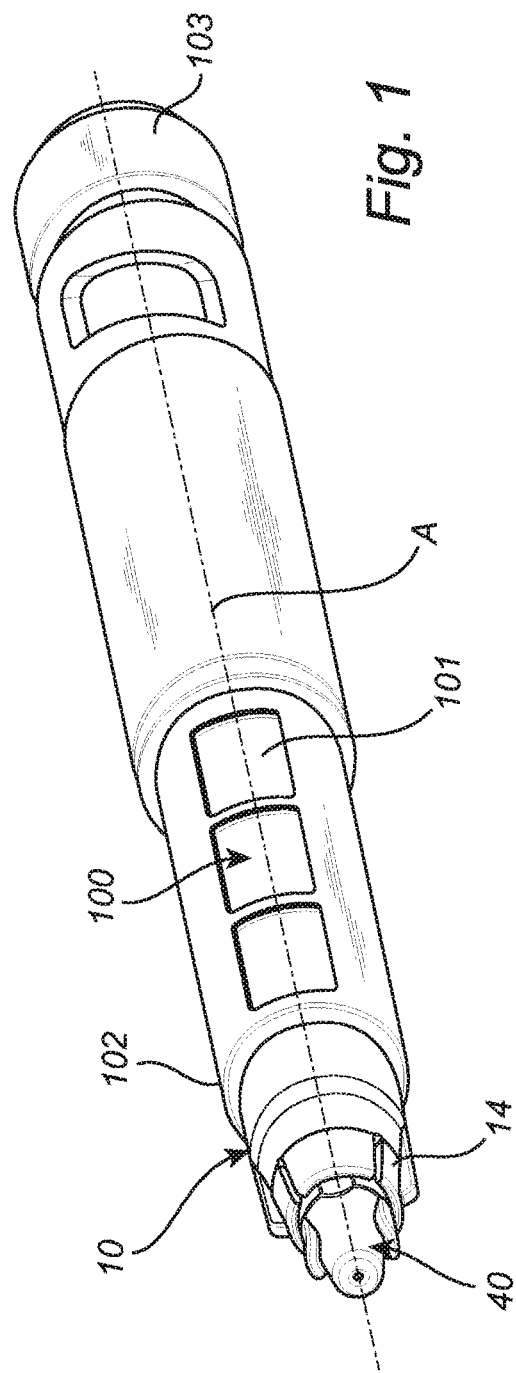

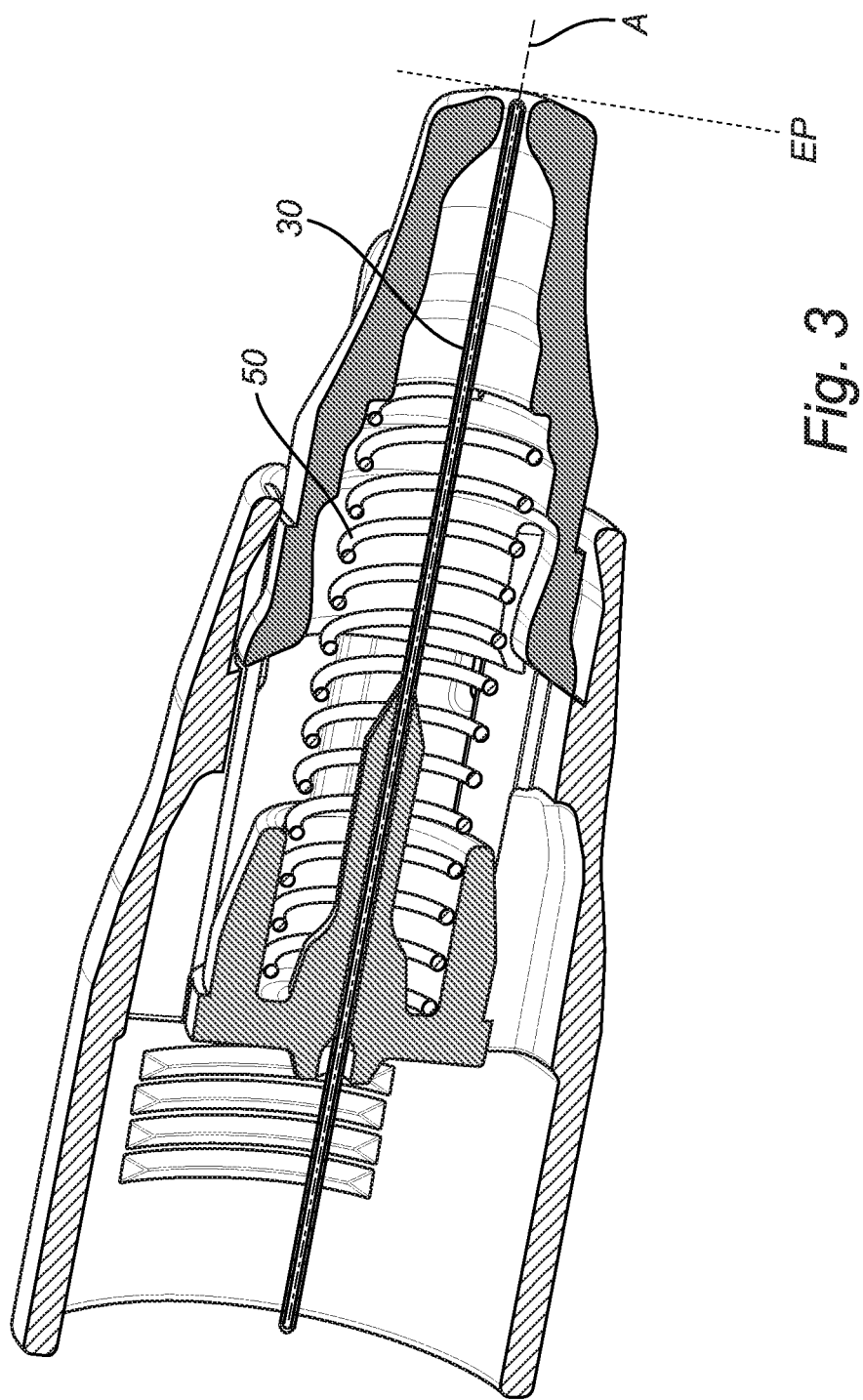

SAFETY INJECTION NEEDLE DEVICE

FIELD OF THE INVENTION

The present invention relates to a safety injection needle device for delivery of a medicament from a storage reservoir.

BACKGROUND OF THE INVENTION

Problems associated with inadvertent needle sticks are well known in the art of blood sampling, percutaneous medication injection and other medical procedures involving use of medical needles. Significant attention has been focused on needle stick problems due to the contemporary sensitivity of exposure to AIDS, Hepatitis and other serious blood-borne pathogen exposures.

Several peoples suffer from different deceases that require frequent medical treatment to ensure that the people's health is maintained at a desired level.

Some diseases, like for example diabetes, requires that insulin is injected at predetermined intervals to maintain the blood sugar of the patient at an acceptable level and to prevent complications and symptoms following from a fluctuating blood sugar levels.

In order to facilitate the daily life of these patients, these patients are often instructed to inject medicament by themselves to eliminate the need for numerous visits at hospitals.

The medicament is enclosed in a container that is fitted in an injection device comprising a needle and injection mechanism to, up on activation, inject the medicament. Preferably the needle is hidden within the injection housing before and after use to prevent an unintentional puncture by the needle. When the content in the container is injected, the container is replaced by a new container and the injection device is once again ready for use. Unfortunately, these injection devices tend to become rather complex and expensive to manufacture.

A second frequently used alternative involves a disposable needle huh that is fitted on a standard type of container containing the medicament. The needle hub is attached to the container to prepare the device for use. Once the medicament is delivered, the needle hub and container are disposed.

However, the used needles might be contaminated and are preferably covered by sonic sort of needle protection device that prevents unintentional punctures or needlesticks and potential transfer of deceases to the user or other persons that might come in contact with the device.

Examples of needle hubs comprising a needle protection devices are disclosed in US 2009221972A and US 2007293819.

There is however still a need for a reliable, less complex needle hub device with a needle protection device that could be manufactured in an efficient way.

SUMMARY OF THE INVENTION

The present invention, defined in the appended claims, relates to a safety injection needle device for delivery of a medicament from a storage reservoir.

The safety injection needle device for delivery of a medicament from a storage reservoir with a longitudinal axis A comprises:

- a device body comprising securing means intended for securing the safety injection needle device to the storage reservoir, a sleeve element extending substantially co-axially to axis A in opposite direction to the securing means for the storage reservoir and having an open forward end, and a needle hub arranged within the sleeve element and extending substantially co-axially to axis A;
- a needle secured in the needle hub and extending co-axially to axis A, said needle comprising a rear end extending from the device body and intended to be arranged within the reservoir once the safety needle device is secured to the storage reservoir, and a forward end extending from the needle hub past the sleeve element of the device body;
- a needle shield device with a forward and rear end movably arranged along axis A within the sleeve element between a retracted position where the tip of the needle is exposed outside de forward end and an extracted position where the tip of the needle is enclosed by the needle shield device, and
- a spring arranged to resilient support the needle shield device such that the needle shield device is forced towards the extracted position, wherein the needle hub has a substantially circular cross sectional shape transverse to axis A with a smaller radius towards the outer end of the needle hub, and the rear end of the needle shield device is made of a deformable material such that at least a section of the rear end of the needle shield device is deformed by the needle hub such that the distance from axis A to the deformed section of the rear end in radial direction from axis A is increased when moved to the retracted position during injection of medicament, and wherein a least one shoulder is formed on the inside wall of the sleeve element such that, after at least a section of the rear end of the needle shield device is deformed and the needle shield device is returned to the extracted position, the deformed section of the rear end of the needle shield device will rest against the shoulder and lock the needle shield device in the extracted position.

The safety injection needle device according to the invention provides the desired protection and avoids accidental puncture or injuries since the needle shield device is enclosing the needle before and after injection. The simple configuration of the safety injection device makes it possible to manufacture and assembly the safety injection needle device in an efficient way which is essential since the safety injection needle device is disposed after use.

The safety injection needle device is preferably used in combination with a standard type of reservoir containing the medicament. The reservoir comprises an opening or a closing element of a permeable material and before injection, the safety injection needle device is secured to the container and the rear end of the needle is arranged in the container, or forced through the closing element to access the interior of the container. In order to prepare the injection device for the injection, the safety injection needle device is arranged substantially transverse to the skin in the desired position of the injection. The needle is still enclosed by the needle shield device.

To start the injection, the reservoir and safety injection needle device are forced against the skin by a force exceeding the force of the spring acting on the needle shield device such that the needle shield device is forced backwards into the sleeve element and the forward end of the needle is exposed and enters the skin. Simultaneously the rear end of the needle shield device is forced against the needle hub such that at least a section of the rear end is permanently deformed and the radius, or distance from axis A to the rear end in radial direction, is increased.

Once the injection is completed, the safety injection needle device and the reservoir are removed from the skin of the patient and the needle shield device is returned by the spring to its extracted position where it encloses the forward end of the needle. The deformed section of the rear end, i.e. the section of the rear end with larger radius or the distance from axis A to the rear end in radial direction, is in the extracted position arranged outside the shoulder on the inside wall of the sleeve element such that the deformed section of the rear end of the needle shield device will be in contact with the shoulder thereby locking the needle shield device in the extracted position and prevent further use of the injection with the safety.

In one embodiment of the device, the needle shield device has a substantially circular cross section transverse to axis A and at least one notch formed in the rear end to facilitate the deformation. The at least one notch divides the annular rear end of the needle shield device into one or more sections that could be deform outwards more easily when forced towards the needle hub. Preferably the number of notches is at least two such that the rear end is divided into two sections, alternatively four notches to divide the rear end into four sections.

In one embodiment of the device, the rear end of the needle shield device is formed of a material that after deformation not return to its original shape. The deformation could be facilitated by selecting a plastic material with a characteristic without memory.

In one embodiment of the device, the rear end of the needle shield device is made of an amorphous thermoplastic material or a plastic material such as polycarbonate, polyimide or polystyrene or a plastic material with a filler material, such as polypropylene with chalk. These materials have characteristics appropriate for this application since the materials, when exposed to a force exceeding a predefined limit, are permanently deformed instead of flexing and returning to its original shape. This deformation could also be named plastic deformation in the meaning that the deformation is irreversible since the material not will retain its original shape.

In one embodiment of the device, the radius of the deformed section of the rear end of the needle shield device is increased, said deformation takes place when the needle shield device is forced towards the needle hub by the force exerted when the injection takes place and the needle shield device is pressed backwards when the needle is injected into the skin.

In one embodiment of the device, an annular recess is formed around the needle in the needle hub and the needle shield device has an open interior such that the one end of the spring is arranged in the annular recess in the needle hub and the other end arranged within the needle shield device. This embodiment of the device makes it possible to fit all the required components within the safety needle device in a space efficient way and reduce the overall size of the device.

In one embodiment of the device, the spring is a helical spring arranged between the needle hub and the needle shield device around the needle. The helical spring with substantially circular cross section is easy to fit within the needle shield device and the recess in needle hub.

In one embodiment of the device, the needle hub has a conical peripheral shape. The conical outer shape provides the desired deformation when the rear end of the needle shield device is forced backwards towards the needle hub.

In one embodiment of the device, the shoulder on the inside wall of the sleeve element is shaped as an annular protrusion extending around the entire inside surface of the sleeve element. The annular protrusion provides efficient support for the deformed section of the rear end and lock the needle shield device after the injection is completed.

In one embodiment of the device, corresponding guiding protrusions and recesses are formed in the inside surface of the sleeve element and the needle protecting device to provide guidance to the needle safety device during movement between the retracted and extracted position. The protrusions and recesses prevents that the needle shield device is turning around axis A in relation to each other which could interfere with the axial movement.

In one embodiment of the device, the shoulder on the inside wall of the sleeve element is angled in relation to a plane transverse to axis A such that the deformed section of the rear end of the needle shield device is forced to remain in contact with the shoulder if a force in the direction towards the retracted position is applied on the needle shield device.

In one embodiment of the device, the distance from axis A to the shoulder on the inside wall of the sleeve element is smaller than the distance from axis A to the deformed rear end of the needle shield device.

The different embodiments described above could all be combined and modified in different ways without departing from the scope of the invention that is defined by the appended claims.

BRIEF DESCRIPTION OF THE DRAWINGS

One embodiment of the safety injection needle device according to the present invention is schematically illustrated in the appended figures.

FIG. 1 illustrates a perspective view of an injection device comprising the safety injection needle device.

FIG. 2*a* illustrates the needle shield device before deformation arranged in an intermediate position between the retracted and extracted position.

FIG. 2*b* illustrates the needle shield device in a position where the deformation is initiated but not completed.

FIG. 2*c* illustrates the needle shield device arranged the retracted position and the deformation completed.

FIG. 2*d* illustrates the needle shield device locked in the extracted position.

FIG. 3 illustrates a cross sectional view of the safety injection needle device through the longitudinal axis A with the spring illustrated.

DETAILED DESCRIPTION

Figure 2A:
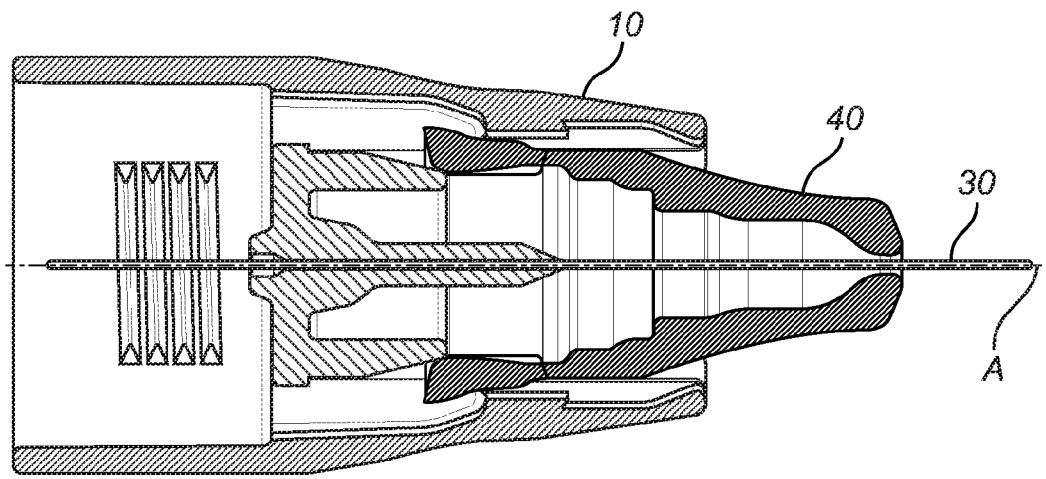
FIGS. 2*a-d* illustrates cross sectional views of the safety injection needle device through the longitudinal axis A to illustrate the characteristic features of the device.

The safety injection needle device 10 is intended to be used in combination with a medicament storage reservoir 100. One example of a storage reservoir, an insulin pen injector, is illustrated in FIG. 1. The reservoir has an elongated reservoir body 101 with a longitudinal axis A. In a forward end 102 of the reservoir an opening is formed. The opening, in the forward end is intended for dispensing of medicament from the reservoir. The opening is closed by a collar element, not illustrated, with a permeable material, for example rubber, arranged in the position of the opening. The opening is substantially circular and arranged co-axially with axis A. The opposite rear end of the reservoir body is shaped like a tube closed by a movable plunger connected to a plunger rod extending co-axially with axis A backwards outside the end of the reservoir body to an activation button 103 or activation mechanism in order for the patient to activate the injection by pressing the activation button and move the plunger towards the opening in the forward end of the reservoir. In figure one a safety injection needle device 10 is secured to the insulin pen 100.

Figure 2B:
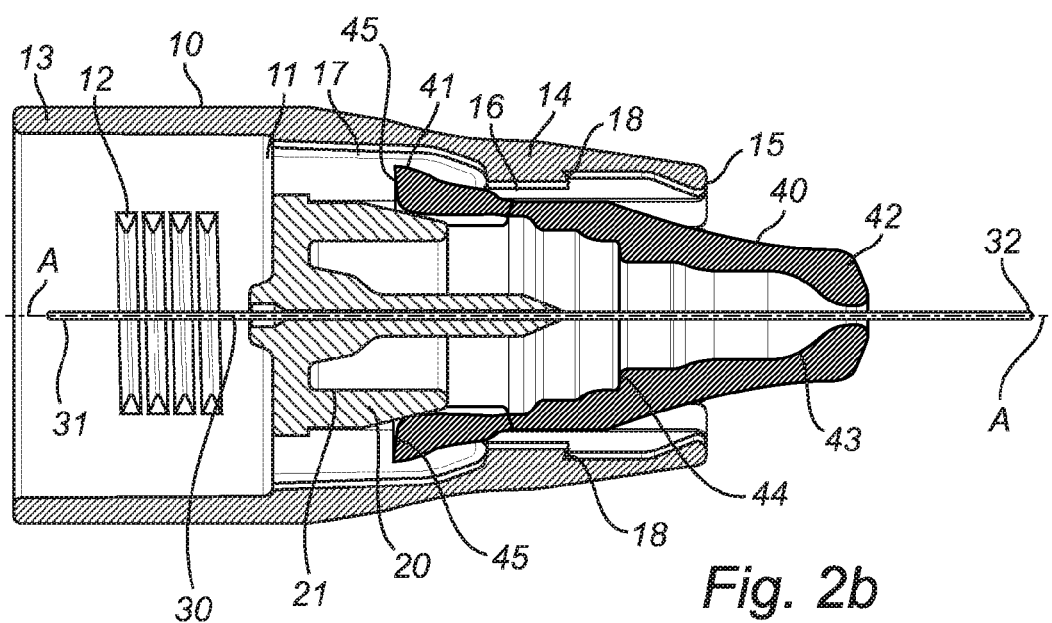
Figure 2C:
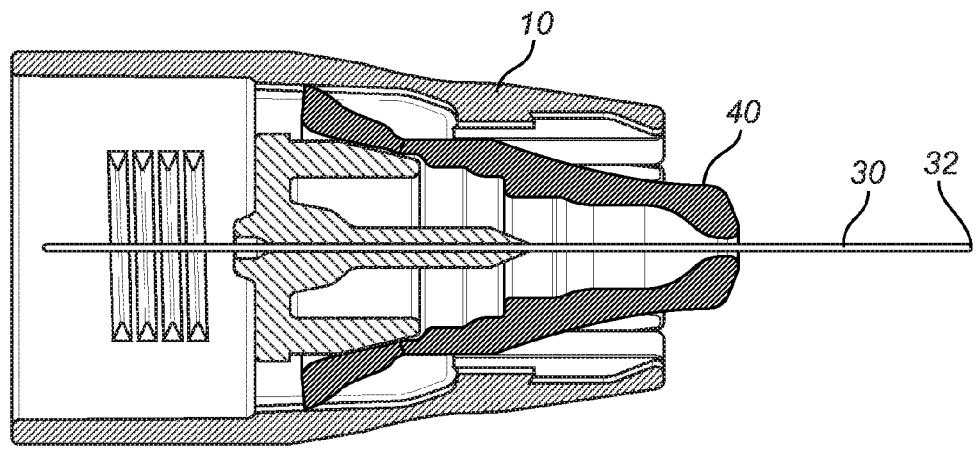
Figure 2D:
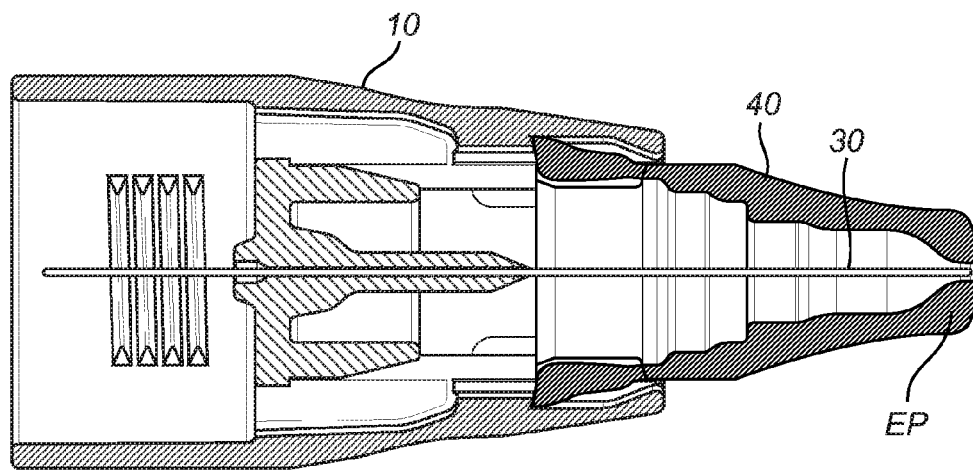

Cross sectional views of the safety injection needle device 10 with the needle shield device in different positions are illustrated in FIGS. 2a to 2d. The configuration of the safety injection needle device is described with reference to these figures.

The safety injection needle device 10 according to the invention comprises a device body 11. In one end of the device body securing means 12 intended for securing the safety needle device 10 to the storage reservoir is arranged. The securing means are embodied as internal treads arranged along the inside of an annular wall 13 intended to enclose the collar element of the storage reservoir. The internal treads are screwed on corresponding treads arranged on the collar element to provide a reliable and rigid securing of the safety injection needle device to the reservoir. However, the securing means could for example also be embodied as snap-fit means designed to be snap-fitted to the collar element of the container.

The device body 11 furthermore comprises a sleeve element 14 extending substantially co-axially to axis A in opposite direction to the annular wall and the securing means. The sleeve element is designed as an elongated sleeve with a substantially circular cross section and a forward open end 15. The outside radius of the sleeve element is reduced towards the forward end. The radius of the cavity formed within the sleeve element is substantially constant along the sleeve such that a cavity 16 for a needle protection device is formed within the sleeve element. In the inward end of the cavity an area 17 with slightly larger radius is formed in the inside surface and in the opposite end of the cavity a shoulder 18 is formed. The shoulder is formed as an annular protrusion extending around the entire cavity in a plane transverse to axis A. The shoulder is facing the open end of the sleeve element and angled in relation to a plane transverse to axis A such that the part of the shoulder arranged closest to the inside surface of the sleeve element is arranged a larger distance from the open end of the sleeve element than the part of the should arranged closer to axis A. The shoulder either has a substantially flat or concave surface.

Within the cavity of the sleeve element, a needle hub 20 is arranged to support a needle 30. The needle hub is arranged in the centre of the cavity within the sleeve element and extending substantially co-axially to axis A. The needle hub has conical shape, i.e. a substantially circular cross sectional shape transverse to axis A with a smaller radius towards the outer end of the needle hub. An annular recess 21 is formed in the outer end of the needle hub co-axial to axis A around the needle in the needle hub such that a central elongated needle support 22 is formed in the centre of the needle hub.

The needle 30 is secured in the needle hub and extending co-axially to axis A. The needle comprises a rear end 31 extending from the device body towards the intended position of the reservoir. The rear end of the needle is forced through the permeable material that is closing the opening in the reservoir when the safety injection needle device is fitted to the reservoir. The forward end 32 of the needle is extending past the open end of the sleeve element. The needle length is selected such that the distance the between the open end of the sleeve element and the tip of the needle corresponds to the desired punctuation depth during injection in order to facilitate injection since the patient only has to press the injection device towards the skin to the position where the sleeve element rests against the skin to achieve the desired punctuation depth.

The safety injection needle device 10 furthermore comprises a needle shield device 40 arranged in the cavity within the sleeve element. The needle shield device has a substantially circular cross sectional shape and is arranged co-axial to axis A. The needle shield device has a conical outer shape with a radius in the rear end 41 corresponding to the radius of the cavity within the sleeve in order to fit within the cavity and to he movable along axis A in relation to the sleeve element. The radius of the needle shield device is reduced towards the forward end 42. Within the centre of the needle shield device a passage 43 extend from the rear to the forward end for the needle. The passage has as larger radius in the rear end of the needle device than in the forward end and a support surface 44 substantially transverse to axis A is formed within the passage. The support surface is facing the rear end of the needle shield device. The needle shield device is movably arranged within the sleeve element along axis A between a retracted position and an extracted position. In the retracted position the forward end of the needle shield device is arranged in the same plane as the open end of the sleeve element, alternatively retracted further into the cavity, and the tip of the needle exposed. In the extracted position the forward end of the needle shield device is extracted to a position where the needle tip is completely enclosed by the needle shield device.

In the illustrated embodiment of the safety injection needle device the needle shield device has a substantially circular rear end but other cross sectional shapes like oval, triangular or square are also possible as long as the sleeve element has a corresponding cross sectional shape.

The rear end is either formed as one element or divided by one or more notches extending substantially parallel to axis A into the needle shield device such that the rear end is formed as one or more sections. The rear end is ended by an end surface 45 arranged substantially transverse to axis A. The rear end of the needle shield device is furthermore provided with two or more bosses, necks or segments extending in substantially radial direction from the surface of the needle shield device. The bosses, necks or segments have a slightly lamer radius than the radius of the open end in the sleeve element to ensure that the needle shield device is maintained within the cavity after assembly of the needle shield device and the compressed spring within the sleeve element.

The rear end 41, or the entire needle shield device, is made of a deformable material that after deformation not retain its original shape. This deformation could also be named plastic deformation in the meaning that the deformation is irreversible since the material not will retain its original shape once deformed. Materials with this feature are amorphous materials and plastic materials with suitable filler material. Examples of materials are poly carbonate, polyamide and polystyrene.

The safety injection needle device 10 furthermore comprises a spring 50 arranged to resilient support the needle shield device such that the needle shield device is forced towards the extracted position. The spring is excluded in FIGS. 2a-2d to more clearly illustrate the surrounding components but is illustrated in FIG. 3. The spring is in the illustrated embodiment embodied as a helical spring with substantially constant radius. The spring has a first end arranged within the annular recess in the needle hub and a second end in contact with the support surface 44 in the passage of the needle shield device to force the needle to the extracted position.

In order to prepare the injection device for injection, the safety injection needle device is fitted on the reservoir and the rear end of the needle entered in the reservoir. When it is time for injection, the patient is arranging the injection device is arranged substantially transverse to the skin with the safety needle device in contact with the skin in the intended injection position. The needle shield device is still arranged in the extracted position and encloses the forward end of the needle.

To start the injection, the injection device, i.e. the reservoir and safety injection needle device, are forced against the skin. The force applied must exceed the force of the spring acting on the needle shield device to move the needle shield device towards the retracted position and the needle into the skin. In order to ensure the desired punctuation depth into the skin, the sleeve element of the safety injection needle device should be in contact with the skin. Once the sleeve element of the safety injection needle device is in contact with the skin the injection of medicament from the reservoir could be initiated either manually by a moving the plunger or automatically by activating a dispensing mechanism that is applying the required pressure on the plunger to dispense medicament from the reservoir via the needle to the patient.

When the needle shield is forced towards the retracted position, the rear end of the needle shield device is forced towards the conical needle hub that, due to its increasing radius closer to its base, will deform at least a section of the rear end. The dimensions of the needle hub radius and the radius of the rear end of the needle shield device are selected such that a permanent deformation is ensured and the radius, or distance from axis A to the end surface of the needle shield device is increased.

Once the injection is completed, the injection device is removed from the skin of the patient. The spring then automatically returns the needle shield device to its extracted position where it encloses the forward end of the needle. The deformed section or sections of the rear end will flex slightly to pass the shoulder extending from the inner surface of the sleeve element to reach the extracted position.

The deformed section, or sections, of the rear end, i.e. the section or sections, of the rear end with larger radius, is in the extracted position arranged outside the shoulder on the inside wall of the sleeve element. Once the needle shield device reaches the extracted position, the end surface of the needle shield device will rest against the shoulder and lock the needle shield device in the extracted position thereby eliminating the risk for unintended punctuation by the used needle.

Before injection has taken place, the needle shield device could be moved a short distance to an intermediate position to verify that the needle is in good condition and ready for use without starting the deformation of the needle shield device. When the needle shield device is released, the spring returns the needle shield device to the extracted position.

The safety injection needle device according could furthermore be provided with corresponding guiding protrusions and recesses formed in the inside surface of the sleeve element and the needle protecting device to guide the movements of the needle shield between the extracted and retracted position. The guiding recesses and protrusions ensure that the intended movement of the needle shield device can take place easily.

All the described and illustrated embodiments of the different parts of the safety injection needle device could however be modified in order to adapt the device to different needs.

The different embodiments described above could all be combined and modified in different ways without departing from the scope of the invention that is defined by the appended claims.

The invention claimed is:

1. Safety injection needle device for delivery of a medicament from a storage reservoir with a longitudinal axis, said device comprising:
   a device body comprising securing means intended for securing the safety injection needle device to the storage reservoir, a sleeve element extending substantially co-axially to the axis in opposite direction to the securing means for the storage reservoir and having an open forward end, and a needle hub arranged within the sleeve element and extending substantially co-axially to the axis;
   a needle secured in the needle hub and extending co-axially to the axis, said needle comprising a rear end extending from the device body and intended to be arranged within the storage reservoir once the safety injection needle device is secured to the storage reservoir, and a forward end extending from the needle hub past the sleeve element of the device body;
   a needle shield device with a forward and rear end movably arranged along the axis within the sleeve element between a retracted position (RP) where the tip of the needle is exposed outside the forward end, and an extracted position (EP) where the tip of the needle is enclosed by the needle shield device, and
   a spring arranged to resiliently support the needle shield device such that the needle shield device is forced towards the extracted position (EP), wherein
   the needle hub has a substantially circular cross sectional shape transverse to the axis with a smaller radius towards an outer end of the needle hub, and the rear end of the needle shield device is made of a plastically deformable material such that at least a section of the rear end of the needle shield device is plastically deformed by the needle hub such that the distance from the axis to the plastically deformed section of the rear end in radial direction from the axis is permanently increased when moved to the retracted position (RP) during injection of medicament, and wherein a least one shoulder is formed on the inside wall of the sleeve element such that, after at least a section of the rear end of the needle shield device is plastically deformed and the needle shield device is returned to the extracted position, the plastically deformed section of the rear end of the needle shield device will rest against the shoulder and lock the needle shield device in the extracted position.

2. The device according to claim 1, wherein the needle shield device has a substantially circular cross section transverse to the axis and at least one notch formed in the rear end to facilitate the plastic deformation.

3. The device according to claim 1, wherein the rear end of the needle shield device is formed of a material that after deformation will not return to its original shape.

4. The device according to claim 1, wherein the rear end of the needle shield device is made of a plastic material.

5. The device according to claim 4, wherein the plastic material includes at least one of polycarbonate, polyamide and polystyrene.

6. The device according to claim 4, wherein the plastic material is an amorphous thermoplastic material.

7. The device according to claim 4, wherein the plastic material further comprises a filler material.

8. The device according to claim 7, wherein the filler material comprises polypropylene with chalk.

9. The device according to claim 1, wherein the distance from the axis to the plastically deformed section of the rear end of the needle shield device after the deformation is increased, said plastic deformation takes place when the needle shield device is forced towards the needle hub by the force exerted when the injection takes place and the needle shield device is pressed backwards when the needle is injected into the skin.

10. The device according to claim 1, wherein an annular recess is formed around the needle in the needle hub and the needle shield device has an open interior such that the one end of the spring is arranged in the annular recess in the needle hub and the other end arranged within the needle shield device.

11. The device according to claim 1, wherein the spring is a helical spring arranged between the needle hub and the needle shield device around the needle.

12. The device according to claim 1, wherein the needle hub has a conical peripheral shape.

13. The device according to claim 1, wherein the shoulder on the inside wall of the sleeve element is shaped as an annular protrusion extending around the entire inside surface of the sleeve element.

14. The device according to claim 1, wherein the shoulder on the inside wall of the sleeve element is angled in relation to a plane transverse to the axis such that the deformed section of the rear end of the needle shield device is forced to remain in contact with the shoulder if a force in the direction towards the retracted position is applied on the needle shield device.

15. The device according to claim 1, wherein corresponding guiding protrusions and recesses are formed in the inside surface of the sleeve element and the needle protecting device to provide guidance to the needle safety device during movement between the retracted and extracted position.

16. The device according to claim 1, wherein the distance from the axis to the shoulder on the inside wall of the sleeve element is smaller than the distance from the axis to the plastically deformed section of the rear end of the needle shield device.

* * * * *